United States Patent [19]

Okamoto et al.

[11] Patent Number: 4,797,417
[45] Date of Patent: * Jan. 10, 1989

[54] FURANONE DERIVATIVES, PROCESS FOR PREPARATION THEREOF AND USE THEREOF

[75] Inventors: Masanori Okamoto, Osaka; Itsuo Uchida, Kyoto; Kazuyoshi Umehara, Ashiya; Masanobu Kohsaka, Sakai; Hiroshi Imanaka, Osaka, all of Japan

[73] Assignee: Fujisawa Pharmaceutical Co., Ltd., Oasak, Japan

[*] Notice: The portion of the term of this patent subsequent to Apr. 29, 2003 has been disclaimed.

[21] Appl. No.: 31,199

[22] Filed: Mar. 27, 1987

Related U.S. Application Data

[63] Continuation of Ser. No. 695,001, Jan. 25, 1985, abandoned, which is a continuation-in-part of Ser. No. 508,892, Jun. 29, 1983.

[30] Foreign Application Priority Data

Jul. 19, 1982 [JP] Japan .................. 57-126599

[51] Int. Cl.$^4$ ............... C07D 307/32; C07D 307/34; A61K 31/365
[52] U.S. Cl. .................... 514/473; 549/214; 549/322; 549/323; 549/313
[58] Field of Search .............. 549/322, 323, 313, 214; 514/473, 461

[56] References Cited

U.S. PATENT DOCUMENTS

| | | | |
|---|---|---|---|
| 3,665,014 | 5/1972 | Fauran et al. | 549/323 |
| 3,826,839 | 7/1974 | Sutton et al. | 514/473 |
| 4,346,102 | 8/1982 | Langlois et al. | 514/473 |
| 4,585,789 | 4/1986 | Okamoto et al. | 514/461 |

FOREIGN PATENT DOCUMENTS 1920176 10/1970 Fed. Rep. of Germany ...... 549/321

*Primary Examiner*—Glennon H. Hollrah
*Assistant Examiner*—Patricia L. Morris
*Attorney, Agent, or Firm*—Oblon, Fisher, Spivak, McClelland & Maier

[57] ABSTRACT

The invention relates to novel furanone derivatives, having an aldose reductase-inhibitory activity, of the formula

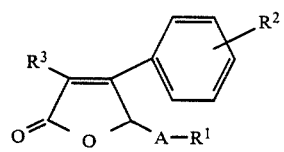

wherein
A is a lower alkylene group,
$R^1$ is a carboxy, hydroxy, protected hydroxy or lower alkoxycarbonyl group,
$R^2$ is a hydrogen or halogen atom or a halo (lower) alkyl group, and
$R^3$ is a hydrogen atom or a hydroxy, carboxy, lower alkoxy or lower alkoxycarbonyl group.

8 Claims, No Drawings

FURANONE DERIVATIVES, PROCESS FOR PREPARATION THEREOF AND USE THEREOF

This application is a continuation of application Ser. No. 695,001, filed on Jan. 25, 1985, now abandoned, which application is a continuation-in-part of application Ser. No. 508,892, filed June 29, 1983.

This invention relates to new furanone derivatives. More particularly, this invention relates to new furanone derivatives and their pharmaceutically acceptable salts which have an aldose reductase-inhivitory activity, to processes for preparation thereof, and to a pharmaceutical composition comprising the same and a method of use thereof.

Accordingly, one object of this invention is to provide the new and useful furanone derivatives and pharmaceutically acceptable salts thereof.

Another object of this invention is to provide processes for preparation of the furanone derivatives and pharmaceutically acceptable salt thereof.

A further object of this invention is to provide a pharmaceutical composition comprising said furanone derivative or a pharmaceutically acceptable salt thereof.

Still further object of this invention is to provide a method of using said furanone derivative or a pharmaceutically acceptable salt thereof for the therapeutic treatment of diabetic complications such as corneal wound healing defects, neuropathy, retinopathy, nephropathy.

The furanone derivatives of this invention are novel and can be represented by the following formula

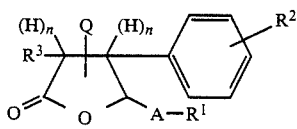

wherein
A is a lower alkylene group,
$R^1$ is a carboxy, hydroxy, protected hydroxy or lower alkoxycarbonyl group,
$R^2$ is a hydrogen or halogen atom or a halo(lower)alkyl group,
$R^3$ is a hydrogen atom or a hydroxy, carboxy, lower alkoxy or lower alkoxycarbonyl group,
Q is the number of double bonds which is equal to 0 or 1, and
n is an integer of 0 or 1,
provided that when Q is 0, then n is 1, when Q is 1, then n is 0, and when $R^3$ is a carboxy or lower alkoxycarbonyl group, then Q is 0.

As to the object compound [I], the following points are to be noted. That is, the object compound [I], wherein Q is 1 and $R^3$ is hydroxy group, can be alternatively represented by its tautomers as shown in the following.

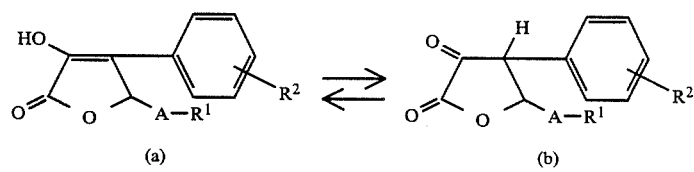

wherein A, $R^1$ and $R^2$ are each as defined above.

In the present specification and claim, however, the said object compound of this invention is represented by the formula (a) only for the convenient sake.

The new furanone derivatives and pharmaceutically acceptable salts thereof can be prepared by the following processes.

Process 1

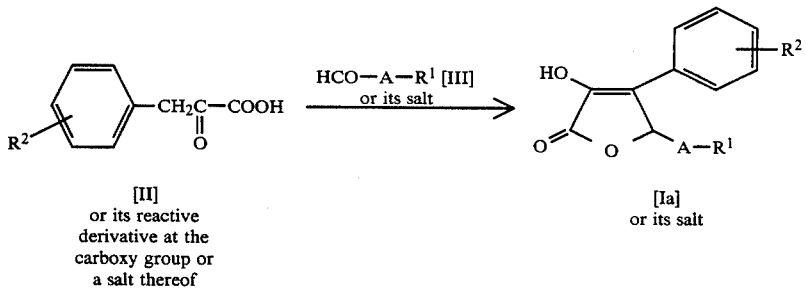

Process 2

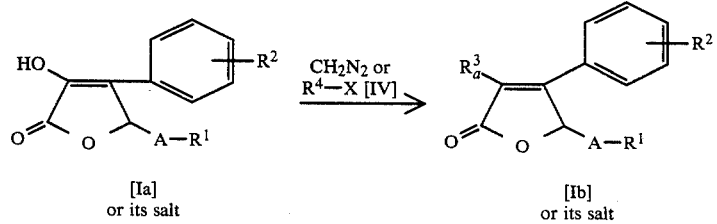

-continued
Process 3
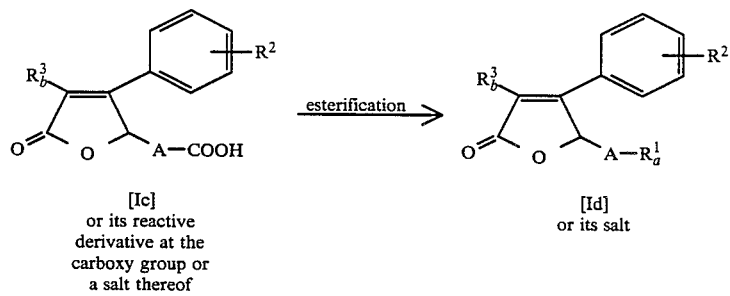
[Ic]
or its reactive
derivative at the
carboxy group or
a salt thereof
[Id]
or its salt
Process 4
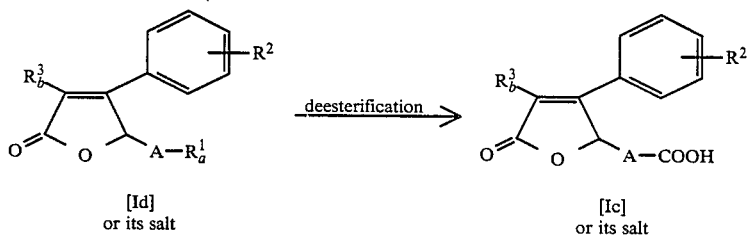
[Id]
or its salt
[Ic]
or its salt
Process 5
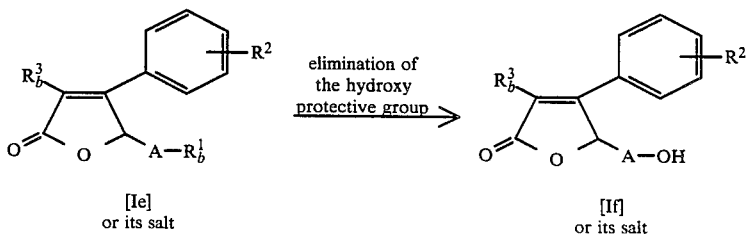
[Ie]
or its salt
[If]
or its salt
Process 6
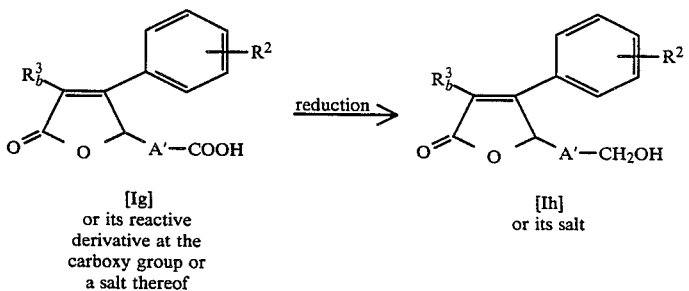
[Ig]
or its reactive
derivative at the
carboxy group or
a salt thereof
[Ih]
or its salt
Process 7
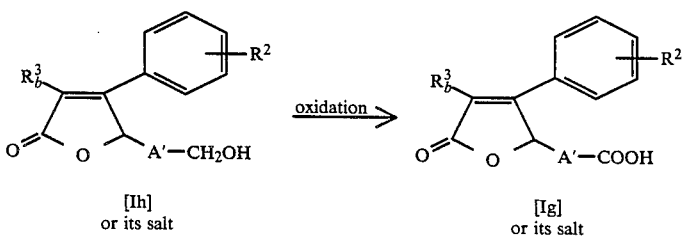
[Ih]
or its salt
[Ig]
or its salt
Process 8

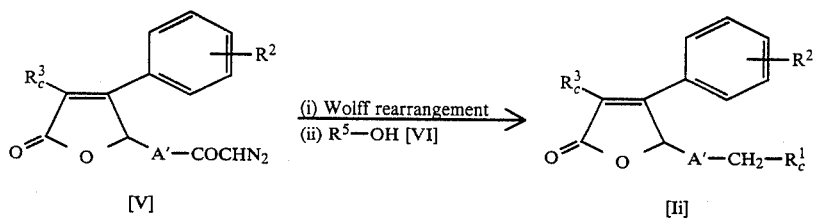

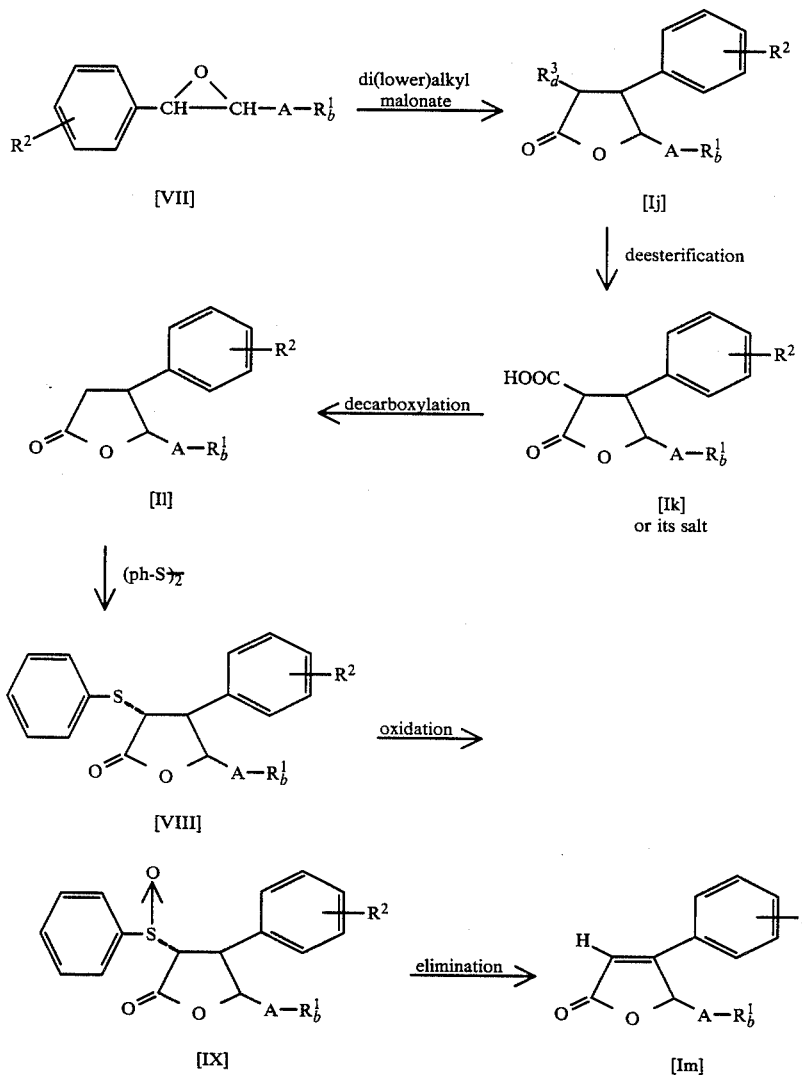

wherein
$R_a^1$ is a lower alkoxycarbonyl group,
$R_b^1$ is a protected hydroxy group,
$R_c^1$ is a carboxy or lower alkoxycarbonyl group,
$R_a^3$ is a lower alkoxy group,
$R_b^3$ is a hydrogen atom or a hydroxy or lower alkoxy group,
$R_c^3$ is a hydrogen atom or a lower alkoxy group,
$R_d^3$ is a lower alkoxycarbonyl group,
$R_5^4$ is a lower alkyl group,
$R^5$ is a hydrogen atom or a lower alkyl group,
A' is a $C_1$-$C_4$ alkylene group,
X is a leaving group, and
$R^1$, $R^2$ and A are each as defined above.

Particulars of the various definitions, which are mentioned hereinabove and hereinafter, and preferred examples thereof are explained in the following.

The term "lower" means a group of 1 to 5 carbon atoms unless otherwise specified.

(1) Re. Lower alkylene group for A and $C_1$-$C_4$ alkylene group for A':

Preferred examples of the alkylene group and $C_1$-$C_4$ alkylene group may include methylene, ethylene, trimethylene, propylene and the like.

(2) Re. Lower alkoxycarbonyl group for $R^1$, $R_a^1$, $R_c^1$, $R^3$ and $R_d^3$:

Preferred examples of the lower alkoxycarbonyl group may include methoxycarbonyl, ethoxycarbonyl, propoxycarbonyl, butoxycarbonyl and the like.

(3) Re. Hydroxy protective group in protected hydroxy group for $R^1$ and $R_b{}^1$:

Preferred examples of the hydroxy protective group may include substituted or unsubstituted alkanoyl (e.g. formyl, acetyl, propionyl, etc.), substituted or unsubstituted aroyl (e.g. benzoyl, etc.), aralkyl (e.g. benzyl, etc.), silyl (e.g. trimethylsilyl, isopropyldimethylsilyl, t-butyldiphenylsilyl, t-butyldimethylsilyl, etc.), tetrahydropyranyl, tetrahydrofuranyl, and the like.

(4) Re. Halogenaatom for $R^2$:

Preferred examples of the halogen may include fluorine, chlorine, bromine, iodine and the like.

(5) Re. Halo(lower)alkyl group for $R^2$:

Preferred examples of the halo(lower)alkyl group may include chloromethyl, bromomethyl, dichloromethyl, 2,2,2-trichloroethyl, trifluoromethyl and the like.

(6) Re. Lower alkoxy group for $R^3$, $R_a{}^3$, $R_b{}^3$ and $R_c{}^3$:

Preferred examples of the lower alkoxy group may include methoxy, ethoxy, propoxy, butoxy, t-butoxy, pentyloxy and the like.

(7) Re. Lower alkyl group for $R^4$ and $R^5$:

Preferred examples of the lower alkyl group may include methyl, ethyl, propyl, isopropyl, butyl, t-butyl, pentyl and the like.

(8) Re. Leaving group for X:

Preferred examples of the leaving group may include halogen (e.g. chlorine, bromine and iodine), sulfonyloxy (e.g. mesyloxy, ethanesulfonyloxy, tosyloxy, benzenesulfonyloxy, etc.), sulfate and the like.

(9) Re. Pharmaceutically acceptable salts of the compound [I]:

Preferred examples of the pharmaceutically acceptable salts of the compound [I] may include alkali metal salts (e.g. sodium salt, potassium salt, etc.), alkaline earth metal salts (e.g. calcium salt, etc.), ammonium salt, ethanolamine salt, triethylamine salt, dicyclohexylamine salt and the like.

In this respect, it is to be noted the compounds [Ia], [Ib], [Ic], [Id], [Ie], [If], [Ig], [Ih]and [Ik] are included within the scope of the compound [I], and accordingly the suitable salts of these compounds [Ia], [Ib], [Ic], [Id], [Ie], [If], [Ig], [Ih]and [Ik] are to be referred to those as exemplified for the object compound [I] mentioned above.

The processes for preparing the object compounds [I] and their salts are explained in detail in the following.

Process 1

The object compound [Ia] and its salt can be prepared by reacting a compound [II] or its reactive derivative at the carboxy group or a salt thereof with a compound [III] or its salt.

Suitable examples of the reactive derivative at the carboxy group of the compound [II] may include ester, activated amide and the like.

Preferred examples of such reactive derivatives may be lower alkyl ester (e.g. methyl ester, ethyl ester, propyl ester, butyl ester, pentyl ester, etc.), aryl ester (e.g. phenyl ester, tolyl ester, etc.), an activated ester with N-hydroxy succinimide, N-hydroxyphthalimide or 1-hydroxy-6-chlorobenzotriazole, an activated amide with imidazole, triazole or dimethylpyrazole, or the like.

Suitable salts of the compound [II] or its reactive derivative at the carboxy group and the compound [III] may include the same as those of the compound [I].

This reaction is usually carried out in a conventional solvent such as water, acetone, dioxane, chloroform, methylene chloride, benzene, toluene, N,N-dimethylformamide or any other organic solvent which does not adversely influence the reaction.

The reaction may be preferably carried out in the presence of a base or acid. Suitable examples of the base may be a conventional ones such as an alkali metal hydroxide (e.g. sodium hydroxide, potassium hydroxide, etc.), an alkali metal carbonate or bicarbonate (e.g. sodium carbonate, potassium carbonate, sodium bicarbonate, potassium bicarbonate, etc.), an alkaline earth metal hydroxide (e.g. calcium hydroxide, etc.), an alkali metal hydride (e.g. sodium hydride, lithium hydride, etc.), an alkali metal amide (e.g. sodium amide, lithium diisopropyl amide, etc.), tri(lower)alkylamine (e.g. trimethylamine, triethylamine, etc.), pyridine or its derivative (e.g. picoline, lutidine, etc.), an organic strong base (e.g. 1,5-diazabicyclo[4.3.0]-non5-ene, 1,4-diazabicyclo[2.2.2.]-octane, 1,8-diazabicyclo[5.4.0]-undec-7-ene, etc.), or the like. Suitable examples of the acid may be a conventional ones such as hydrochloric acid, hydrobromic acid, sulfuric acid, p-toluenesulfonic acid or the like.

The reaction temperature is not critical, and the reaction is usually carried out under cooling, at ambient temperature or under warming or heating.

Process 2

The object compound [Ib] and its salt can be prepared by reacting a compound [Ia] or its salt with diazomethane or a compound [IV].

Suitable examples of the compound [IV] maY be lower alkyl halide (e.g. methyl iodide, ethyl iodide, propyl iodide, butyl iodide, butyl chloride, pentyl chloride, etc.), lower alkyl sulfonate (e.g. methyl benzenesulfonate, ethyl mesylate, etc.), di(lower)alkyl sulfate (e.g. dimethyl sulfate, diethyl sulfate, etc.) or the like.

This reaction is usually carried out in a conventional solvent such as water, methanol, ethanol, tetrahydrofuran, dioxane, methylene chloride, N,N-dimethylformamide, dimethyl sulfoxide, or any other organic solvent which does not adversely influence the reaction. In case that the above-mentioned compound [IV] is liquid, it can be also used as a solvent.

When the compound [IV] is used in this process, this reaction is preferably carried out in the presence of a conventional base. Suitable examples of the base may include the same as those mentioned in the description of the foregoing Process 1.

The reaction temperature is not critical, and the reaction can be carried out under cooling, at ambient temperature or under warming or heating.

Process 3

The object compound [Id] and its salt can be prepared by subjecting a compound [Ic] or its reactive derivative at the carboxy group or a salt thereof to an esterification reaction.

Suitable examples of the reactive derivative at the carboxy group of the compound [Ic] may be a conventional ones such as acid halide (e.g. acid chloride, acid bromide, etc.); a mixed acid anhydride with an acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; or the like. These reactive derivatives can optionally be selected and used according to the kind of the compound [Ic].

Suitable salts of the reactive derivative may include the same as those of the compound [I].

The esterifying agents to be used in this process may include a conventional ones such as lower alkanol (e.g. methanol, ethanol, propanol, butanol, etc.) or its reactive equivalent (e.g. halide, sulfonate, sulfate, etc.), or the like.

This reaction is usually carried out in a conventional solvent which does not influence the reaction, such as acetone, tetrahydrofuran, dioxane, methylene chloride, benzene, toluene, xylene, N,N-dimethylformamide, dimethyl sulfoxide, pyridine or the like. In case that the above-mentioned esterifying agents is liquid, it can be also used as a solvent.

In case that the lower alkanol is used as the esterifying agent and the compound [Ic] is used in a free acid form, this reaction may be preferably carried out in the presence of an acid as exemplified in the foregoing Process 1. And in case that the reactive equivalent of the lower alkanol is used as the esterifying agent or the compound [Ic] is used in the reactive derivative form, this reaction may be preferably carried out in the presence of a base as exemplified in the foregoing Process 1.

The reaction temperature is not critical, and the reaction can be carried out under cooling, at ambient temperature or under warming or heating.

Process 4

The object compound [Ic] and its salt can be prepared by subjecting a compound [Id] or its salt to a deesterification reaction.

This reaction is carried out in accordance with a conventional method such as hydrolysis, reduction or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4,3,0]-non-5-ene, 1,4-diazabicyclo[2,2,2]octane, 1, 5,4,0]undec-7-ene, or the like. Suitable acid may include an organic acid [e.g. formic acid, acetic acid, propionic acid, trichloroacetic acid, trifluoroacetic acid, etc.] and an inorganic acid [e.g. hydrochloric acid,hydrobromic acid, sulfuric acid, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable to this process may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the abovementioned acids to be used in chemical reduction are in liquid, they can also be used as a solvent. Further, a suitable solvent to be used in catalytic reduction may be the abovementioned solvent, and other conventional solvent such as diethyl ether, dioxane, tetrahydrofuran, etc., or a mixture thereof.

The reaction temperature of this reduction is not critical and the reaction is usually carried out under cooling to warming.

Process 5

The object compound [If] and its salt can be prepared by subjecting a compound [Ie] or its salt to an elimination reaction of the hydroxy protective group.

This reaction can be carried out substantially in the same manner as that of the foregoing Process 4 (i.e. hydrolysis and reduction). Therefore, the reaction mode and reaction conditions (e.g. solvent, acid, base catalyst, reaction temperature, etc.) can be referred to those as illustrated in the foregoing Process 4.

Process 6

The object compound [Ih] and its salt can be prepared by reducing a compound [Ig] or its reactive derivative at the carboxy group or a salt thereof.

Suitable salts of the reactive derivative of the compound [Ig] may include the same as those of the compound [I], exemplified previously.

In this process, the compound [Ih] and its salt can be prepared (1) by reacting the compound [Ig] or its reactive derivative at the carboxy group or a salt thereof directly with a reducing agent such as lithium aluminum hydride, or, more preferably, (2) by reacting the compound [Ig] or its salt with a carboxy-activating agent such as an alkyl halocarbonate (e.g. methyl chlorocarbonate, ethyl chlorocarbonate, etc.) and then with a reducing agent such as alkali metal borohydride (e.g. lithium borohydride, lithium cyanoborohydride, sodium borohydride, potassium borohydride, sodium cyanoborohydride, etc.).

This reaction is conducted in a conventional solvent such as methanol, ethanol, dioxane or tetrahydrofuran under ice-cooling, at ambient temperature, or at an intermediate temperature.

In the latter method (2), good results are obtained in most cases where the reaction is carried out in the presence of a base. Preferred examples of the base may include the same as mentioned in the description of the foregoing Process 1.

Process 7

The object compound [Ig] and its salt can be prepared by oxidizing a compound [Ih] or its salt.

Suitable examples of the oxidizing agent may include Jones reagent, peracid (e.g. peracetic acid, perbenzoic acid, m-chloroperbenzoic acid, etc.), chromic acid, potassium permanganated and the like.

This reaction is preferably conducted in a solvent inert to the reaction, such as acetone, dimethylformamide, or methylene chloride, under cooling or at ambient temperature.

Process 8

The object compound [Ii] and its salt can be prepared by the following methods.

Namely, (1) the compound [V] is first subjected to so called Wolff rearrangement reaction so as to convert the diazomethylcarbonyl group to isocyanatomethyl group, and then (2) reacting the resultant product with the compound [VI].

In the first step, Wolff rearrangement reaction is usually carried out in the presence of a catalyst such as silver compound (e.g. silver oxide, silver benzoate, etc.), alkali metal thiosulfate (e.g. sodium thiosulfate, potassium thiosulfate, etc.), alkali metal hydroxide (e.g. sodium hydroxide, potassium hydroxide, etc.), tertiay amine (e.g. triethylamine, etc.) or the like; or carried out by exposing the compound [V] to arc lamp.

This reaction is usually carried out in a solvent which does not adversely influence the reaction, such as water, methanol, ethanol, dioxane tetrahydrofuran, acetic acid or the like. The reaction temperature is not critical, and the reaction is usually carried out under cooling to warming.

The reaction product (i.e. isocyanatomethyl compound) thus obtained is, with or without isolation thereof, reacted with the compound [VI]. The reaction solvent and the reaction temperature in this step (2) can be referred to those as exemplified in the above step (1).

Process 9

The object compound [Im] can be prepared by the following steps.

Namely, the compound [Im] is prepared by first reacting the compound [VII] with di(lower)alkyl malonate (step 1), subjecting the resultant product (i.e. compound [Ij]) to a deesterification reaction (step 2), subjecting the resultant product (i.e. compound [Ik]) to a decarboxylation reaction (step 3), reacting the resultant product (i.e. compound [Il]) with diphenyl disulfide in the presence of a base (step 4), subjecting the resultant product (i.e. compound [VIII]) to an oxidation reaction (step 5), and then subjecting the resultant product (i.e. compound [IX]) to an elimination reaction (step 6).

Detailed explanation of the above steps is as follows :
(1) step 1:

The compound [Ij] can be prepared by reacting the compound [VII] with di(lower)alkyl malonate in the presence of a base.

Suitable examples of the di(lower)alkyl malonate may be dimethyl malonate, diethyl malonate, dipropyl malonate, ethyl methyl malonate or the like.

Suitable examples of the base may include alkali and alkaline earth metal hydroxides, carbonates or bicarbonates (e.g. sodium hydroxide, potassium hydroxide, calcium hydroxide, sodium carbonate, calcium carbonate, sodium bicarbonate, etc.), ammonium hydroxide, amines (e.g. methylamine, ethylamine, diethylamine, trimethylamine, etc.) and the like.

This reaction is preferably conducted in a solvent inert to the reaction, such as methanol, ethanol, or propanol, at ambient temperature or under heating up to the refluxing temperature.

(2) step 2:

The compound [Ik] and its salt can be prepared by subjecting a compound [Ij] to a deesterification reaction.

The reaction can be carried out substantially in the same manner as that of the foregoing Process 4, and therefore the reaction mode and reaction conditions (e.g. solvent, base, acid, catalyst, reaction temperature, etc.) can be referred to those as exemplified in the foregoing Process 4.

(3) step 3:

The compound [Il] can be prepared by subjecting a compound [Ik] or its salt to a decarboxylation reaction.

This reaction is usually carried out by heating the compound [Ik] or its salt in the absence or presence of a solvent which does not adversely influence the reaction and has somewhat high boiling point, such as toluen, xylene, N,N-dimethylformamide, dimethyl sulfoxide or the like.

(4) step 4:

The compound [VIII] can be prepared by reacting a compound [Ik] with diphenyl disulfide in the presence of a base.

Suitable bases to be used in this reaction may be an organometallic compound (e.g. butyl lithium, phenyl lithium, phenyl sodium, lithium diisopropylamide, lithium bistrimethylsilylamide, etc.), metal hydride (e.g. sodium hydride, lithium hydride, etc.), alkali metal alkoxide (e.g. sodium methoxide, sodium ethoxide, potassium ethoxide, etc.) or the like.

This reaction is usually carried out in a solvent which does not adversely influence the reaction, such as tetrahydrofuran, dioxane, benzene, toluene or the like.

The reaction temperature is not critical, and the reaction is usually carried out under cooling, at ambient temperature or under warming.

(5) step 5:

The compound [IX] can be prepared by subjecting a compound [VIII] to an oxidation reaction.

This reaction can be carried out in substantially the same manner as that of the foregoing Process 7, and therefore the reaction mode and the reaction conditions (e.g. oxidizing agent, solvent, reaction temperature, etc.) can be referred to those as exemplified in the foregoing Process 7.

(6) step 6:

The compound [Im] can be prepared by subjecting a compound [IX] to an elimination reaction of the phenylsulfinyl goup.

This reaction is usually carried out by heating the compound [IX] in the absence or presence of a solvent which does not adversely influence the reaction and has somewhat high boiling point, such as toluene, xylene, N,N-dimethylformamide, dimethyl sulfoxide, 1-butanol or the like.

The object compounds [I] obtained by the above processes can be isolated and purified by a conventional manner such as recrystallization, reprecipitation, column chromatography or the like.

Among the starting compounds [II], [V] and [VII], new compounds can be prepared by the methods of Preparations mentioned later and any process known in the art for preparing structurally analogous compounds thereto.

It is to be noted that each of the object compound [I] and the starting compounds [II] to [IX] may include one or more stereoisomers due to asymmetric carbon atoms in the molecule, and all of such isomers of the compounds [I] to [IX] are included within the scope of this invention.

The new furanone derivatives [I] and their pharmaceutically acceptable salts have been found to possess aldose reductase-inhibiting activity and are of value, for example as drugs for the treatment of diabetic cataract and neuropathy.

The aldose reductase-inhibiting activity values of some representative species of the furanone derivatives [I] are given below.

(1) Enzymatic assay method:

| | |
|---|---|
| 0.5 M Phosphate buffer (pH 6.2) | 0.1 ml |
| 2.0 M Lithium sulfate | 0.2 ml |
| The compound of this invention (dissolved in physiological saline solution) | 0.1 ml |
| Enzyme solution [aldose reductase solution, prepared as described below (2)] | 0.5 ml |
| 60 mM D,L-glyceraldehyde | 0.1 ml |
| 2.5 mM Nicotineamide adenine dinucleotide phosphate (reduced form) (NADPH) | 0.1 ml |

The above reactants were mixed and reacted at 35° C. for 2 minutes and the decrease in amount of NADPH was measured with an Automatic Reaction Rate Analyzer Model LKB-8600 of LKB Producter A. B. The enzyme activity at achange in absorbance of 0.001 per minute was taken as unity.

(2) Method for preparing an enzyme solution

Rabbit eyes were enucleated and the lenses collected. The lenses were homogenized with 3 volumes of distilled water at 4° C. (All the subsequent procedures were also performed at 4° C.) and centrifuged at 10,000 G for 60 minutes. The supernatant was dialyzed against 2 liters of 0.05 M of saline solution and the interall fluid was used as the enzyme solution.

The results are shown in the following table. Each IC50 value (M) represents the concentration of the compound of this invention at which the aldose reductase activity is inhibited by 50%.

| Test Compound (Example No.) | IC$_{50}$ (M) |
|---|---|
| 4 | $2.2 \times 10^{-7}$ |
| 17 | $5.0 \times 10^{-8}$ |
| 18 | $2.2 \times 10^{-7}$ |
| 19 | $1.5 \times 10^{-7}$ |
| 20 | $4.8 \times 10^{-7}$ |
| 22 | $2.0 \times 10^{-7}$ |
| 29-8 | $5.4 \times 10^{-7}$ |

-continued

| Test Compound (Example No.) | IC$_{50}$ (M) |
|---|---|
| 30-2 | $2.5 \times 10^{-6}$ |
| 30-3 | $5.4 \times 10^{-7}$ |

The new furanone derivatives [I] and their pharmaceutically acceptable salts of this invention can be used as pharmaceutical compositions for the treatment of diabetic cataract and/or neuropathy. The pharmaceutical composition is provided in various forms such as solid preparations, semi-solid preparation or liquid preparations, which contain the active compound of this invention, i.e., the compound [I] or a pharmaceutically acceptable salt thereof, together with an organic or inorganic carrier or/and excipient suitable for external, internal or local administration. This active component is used in combination with harmless and pharmacologically acceptable auxiliary components to provide such suitable dosage form as tablets, pellets, capsules, suppositories, solutions, emulsions, suspensions, etc. Examples of such auxiliary components include those which can be effectively utilized in the production of solid, semisolid or liquid preparations, for example, water, glucose, lactose, gelatin, mannitol, starch paste, magnesium trisilicate, corn starch, keratin, colloidal silica, potato starch, urea, etc. Furthermore, such auxiliaries as stabilizers, extenders, colorants and fragrances may also be incorporated. The pharmaceutical compositions according to this invention may also contain preservatives so that the activity of the active component can be preserved. Said compositions should contain the active component in an amount sufficient for the production of desirable therapeutic effects against the progress or actual condition of a disease concerned.

When the pharmaceutical compositions are applied to humans, they are desirably administered by the intravenous, intramuscular or oral route. The effective dose of each active substance depends on the age and/or symptom of the patient to be treated. Generally, however, the pharmaceutical preparations contain about 50 mg, 100 mg, 250 mg or 500 mg of the active substance per unti dosage form and are administered to humans or animals at a daily dose of 0.1–100 mg per kilogram of body weight. 35 The following preparations and examples illustrate this invention in more detail.

PREPARATION 1

A solution of 3-(4-methoxy-5-oxo-3-phenyl-2,5-dihydro-2-furyl)propionic acid (500 mg) in thionyl chloride (2 ml) was heated at 70° C. with stirring for 1 hour. After cooling, the solvent was removed under the reduced pressure to give a residue which was taken up in methylene chloride. To this solution was added dropwise a solution of diazomethane in diethyl ether. The solvent was removed under the reduced pressure to give 5-(4-diazo-3-oxobutyl)-3-methoxy-4-phenyl-2(5H)furanone (465 mg) which was recrystallized from diisopropyl ether.

mp: 70° C. (dec.)

IR (CHCl$_3$) 3100, 2100, 1750, 1640 cm$^{-1}$.

NMR (CDCl$_3$, δ): 1.4–2.0 (1H, m), 2.3–2.8 (3H, m), 4.08 (3H, s), 5.27 (1H, s), 5.42 (1H, dd, J=2, 8 Hz), 7.3–7.8 (5H, m).

PREPARATION 2

3-Chloroperbenzoic acid (2.14 g) was added to a solution of 5-(t-butyldiphenylsilyloxy)-1-phenyl-1-pentene (3.30 g) in dichloromethane (65 ml) at ambient temperature and the resulting mixture was stirred at the same temperature for 2 hours. The reaction mixture was poured into a mixture of diethyl ether and 5% aqueous sodium bisulfite (100 ml). The organic layer was separated, washed with aqueous sodium bicarbonate, water and brine, dried over magnesium sulfate, and evaporated in vacuo to give (2R*, 3R*)-3-[3-(t-butyldiphenylsilyloxy)propyl]-2-phenyloxirane (3.45 g) as an oil.

NMR (CDCl$_3$, δ): 1.05 (9H, s), 1.3-1.9 (4H, m), 3.5-4.2 (4H, m), 7.2-7.8 (15H, m).

EXAMPLE 1

A mixture of methyl 3-(4-chlorophenyl)-2,2dimethoxypropionate (6.09 g) and formic acid (27 ml) was heated at 65 to 70° C. for 4 hours with stirring. The reaction mixture was cooled and extracted with methylene chloride. The extract was washed with water, dried over magnesium sulfate and evaporated in vacuo to give methyl 3-(4-chlorophenyl)propionate.

To a solution of 3-(4-chlorophenyl)propionate obtained above and ethyl 3-formylpropionate (2.91 ml) in N,N-dimethylformamide (64 ml) was dropwise added 1,8-diazabicyclo[5.4.0]undecen-7 (2.83 ml) at 0° C. over a period of 2 minutes. The mixture was stirred at the same temperature for 2.5 hours and the solvent was evaporated in vacuo. To the residue was added 1N hydrochloric acid and the mixture was extracted with ethyl acetate. The extract was washed with water, dried and evaporated in vacuo. The residue was recrystallized from diisopropyl ether to give ethyl 3-[3-(4-chlorophenyl)-4-hydroxy-5-oxo-2,5-dihydro-2-furyl]propionate (3.33 g).

IR (Nujol) : 3300, 1745, 1730, 1675 cm$^{-1}$.

EXAMPLE 2

Ethyl 3-[4-hydroxy-5-oxo-3-(3-trifluoromethylphenyl)2,5-diydro-2-furyl]propionate was obtained according to a similar manner to that of Example 1.

IR (Nujol) : 3300, 1740, 1675 cm$^{-1}$.

EXAMPLE 3

To a solution of methyl 2-oxo-3-phenylpropionate (2.0 g) and 3-benzyloxypropanal (1.84 g) in N,N-dimethylformamide (40 ml) was dropwise added 1,8-diazabicyclo[5.4.0]undecen-7 (1.76 ml) at 0° C. with stirring. The mixture was stirred at the same temperature for 2 hours and the solvent was evaporated. The residue was added to diluted hydrochloric acid and extracted with diethyl ether. The extract was washed with water, dried and evaporated in vacuo. The residue was recrystallized from diisopropyl ether to give 3-hydroxy-4-phenyl-5(2-benzyloxyethyl)-2(5H)furanone (2.39 g).

IR (CH$_2$Cl$_2$): 3480, 1755 cm$^{-1}$

NMR (CDCl$_3$, δ): 1.5-2.0 (1H, m), 2.1-2.7 (1H, m), 3.6-3.8 (2H, m), 4.53 {2H, s), 5.62 (1H, dd, J=2, 8 Hz), 7.90 (1H, br s), 7.32 (5H, s), 7.3-7.8 (5H, m).

EXAMPLE 4

To a mixture of ethyl 3-(4-hydroxy-5-oxo-3-phenyl-2,5-dihydro-2-furyl)propionate (86 g) and potassium carbonate (51.62 g) in N,N-dimethylformamide (855 ml) was added dropwise methyl iodide (23.25 ml) at ambient temperature with stirring and the mixture was stirred for 2.5 hours at the same temperature. The solvent was evaporated in vacuo to give a residue which was poured into diluted hydrochloric acid and extracted with ethyl acetate. The extract was washed with water and brine successively and dried. Evaporation of the solvent gave ethyl 3-(4-methoxy-5-oxo-3-phenyl-2,5-dihydro-2-furyl)propionate which was recrystallized from diisopropyl ether (73.07 g).

mp : 41-42° C.

IR (Nujol) : 1750, 1720, 1650 cm$^{-1}$.

NMR (CDCl$_3$, δ) : 1.25 (3H, t, J=7 Hz), 1.50-1.96 (1H, m), 2.1-2.75 (3H, m), 4.12 (3H, s), 4.32 (2H, q, J=7 Hz), 5.50 (1H, dd, J=2, 8 Hz), 7.27-7.82 (5H, m)

EXAMPLE 5

Ethyl 3-(5-oxo-3-phenyl-4-propoxy-2,5-dihydro-2furyl)propionate was obtained according to a similar manner to that of Example 4.

IR (CHCl$_3$) 2960, 1745, 1640, 1155, 1095 cm$^{-1}$.

NMR (CDCl$_3$, δ): 0.97 (3H, t, J=7 Hz), 1.23 (3H, t, J=7 Hz), 1.48-2.03 (3H, m), 2.13-2.70 (3H, m), 4.13 (2H, q, J=7 Hz), 4.20-4.67 (2H, m), 5.45 (1H, dd, J=2, 8 Hz), 7.27-7.87 (5H, m).

EXAMPLE 6

Ethyl 3-(4-butoxy-5-oxo-3-phenyl-2,5-dihydro-2furyl)propionate was obtained according to a similar manner to that of Example 4.

IR (CHCl$_3$) 2950, 1745, 1640, 1150, 1100 cm$^{-1}$.

NMR (CDCl$_3$, δ): 0.93 (3H, t, J=7 Hz), 1. t, J=7 Hz), 1.37-2.00 (5H, m), 2.13-2.70 (3H, m), 4.13 (2H, q, J=7 Hz), 4.20-4.60 (2H, m), 5.47 (1H, dd, J=2, 8 Hz), 7.27-7.83 (5H, m).

EXAMPLE 7

Ethyl 3-(5-oxo-4-pentyloxy-3-phenyl-2,5-dihydro2-furyl)propionate :;as obtained according to a similar manner to that of Example 4.

IR (film) : 1755, 1740, 1645 cm$^{-1}$.

NMR (CDCl$_3$, δ): 0.77-2.00 (13H, m), 2.17-2.77 (3H, m), 4.17 (2H, q, J=8 Hz), 4.30-4.67 (2H, m), 5.48 (1H, dd, J=2, 8 Hz), 7.37-7.88 (5H, m).

EXAMPLE 8

Ethyl 3-[3-(4-chlorophenyl)-4-methoxy-5-oxo-2,5-dihydro-2-furyl]propionate was obtained according to a similar manner to that of Example 4.

IR (film) : 1750, 1730, 1645, 1590 cm$^{-1}$.

NMR (CDCl$_3$, δ): 1.27 (3H, t, J=7 Hz), 1.43-1.93 (1H, m), 2.20-2.80 (3H, m), 4.13 (3H, s), 4.17 (2H, q, J=7 Hz), 5.43 (1H, dd, J=2, 8 Hz), 7.45 (2H, d, J=9 Hz), 7.68 (2H, d, J=9 Hz).

EXAMPLE 9

Ethyl 3-[4-methoxy-5-oxo-3-(3-trifluoromethylphenyl)-2,5-dihydro-2-furyl]propionate was obtain according to a similar manner to that of Example 4.

IR (film) : 1760, 1735, 1650 cm$^{-1}$.

NMR (CDCl$_3$, δ): 1.27 (3H, t, J=7 Hz), 1.47-1.97 (1H, m), 2.10-2.80 (3H, m), 4.17 (2H, q, J=7 Hz), 4.18 (3H, s), 5.48 (1H, dd, J=2, 9Hz), 7.58-8.12 (4H, m).

EXAMPLE 10

3-Methoxy-4-phenyl-5-(2-benzyloxyethyl)-2(5H)furanone was obtained according to a similar manner to that of Example 4.

IR (CH$_2$Cl$_2$): 1750 cm$^{-1}$.

NMR (CDCl$_3$, δ): 1.65 (1H, ddd, J=4, 9, 18 Hz), 2.32 (1H, dddd, J=2, 6, 12, 18 Hz), 3.5–3.8 (2H, m), 4.07 (3H, s), 4.52 (2H, s), 5.55 (1H, dd, J=2, 9 Hz), 7.33 (5H, s), 7.2–7.7 (5H, m).

EXAMPLE 11

A mixture of methyl 3-(4-hydroxy-5-oxo-3-phenyl2,5-dihydro-2-furyl)propionate (262 mg), ethyl iodide (234 mg) and potassium carbonate (207 mg) in dimethylformamide (3 ml) was stirred for 3.5 hours at ambient temperature. The mixture was poured into a mixture of dichloromethane (10 ml) and water (10 ml). The separated organic layer was washed with water three times, dried and evaporated to dryness. The oily residue was purified by column chromatography on silica gel (8 g, elution by benzene) to yield methyl 3-(4-ethoxy-5-oxo-3-phenyl-2,5-dihydro-2-furyl)propionate (0.20 g) as an oil.

IR (film): 1750 (br), 1650 cm$^{-1}$.
Mass: 290 (M+).

EXAMPLE 12

Methyl 3-(4-propoxy-5-oxo-3-phenyl-2,5-dihydro-2furyl)propionate was obtained according to a similar manner to that of Example 11.

IR (film) : 1740, 1645 cm$^{-1}$.
Mass: 304 (M ).

EXAMPLE 13

Methyl 3-(4-butoxy-5-oxo-3-phenyl-2,5-dihydro-2furyl)propionate was obtained according to a similar manner to that of Example 11.

IR (film): 1750, 1650 cm$^{-1}$.
Mass: 318 (M ).

EXAMPLE 14

To a solution of 3-(4-hydroxy-5-oxo-3-phenyl-2,5-dihydro-2-furyl)propionic acid (80 g) in ethanol (3.2 () was added dropwise conc. sulfuric acid (160 ml) over a period of 0.5 hour and the mixture was stirred for 2.5 hours at ambient temperature. Evaporation of ethanol gave a residue which was poured into ice-cold water (2.4 () and extracted with chloroform. The extract was washed with water and brine successively and evaporated to dryness to give ethyl 3-(4-hydroxy-5-oxo-3-phenyl2,5-dihydro-2-furyl)propionate which was recrystallized from diisopropyl ether (87.05 g).

mp: 114.5–115.5° C.
IR (Nujol) : 3270, 1745, 1710, 1670 cm$^{-1}$.
NMR (CDCl$_3$, δ): 1.22 (3H, t, J=7 Hz), 1.48–2.13 (1H, m), 2.17–2.93 (3H, m), 4.22 (2H, q, J=7 Hz), 5.57 (1H, dd, J=2, 8 Hz), 7.17–8.0 (5H, m).

EXAMPLE 15

To a solution of 3-(4-hydroxy-5-oxo-3-phenyl2,5-dihydro-2-furyl)propionic acid (3.85 g) in dry methanol (60 ml) was added conc. sulfuric acid (3.8 ml) in one portion at 5° C. After stirring for 3 hours at ° C., the mixture was poured into a mixture of water (100 ml) and dichloromethane (50 ml). The aqueous layer was extracted with dichloromethane (50 ml) once again. The combined organic layers were washed with water three times, dried, and evaporated to dryness. To the residue was added diethyl ether and the solid was collected by filtration to yield methyl 3-(4-hydroxy-5-oxo-3-phenyl-2,5-dihydro-2-furyl)propionate (3.49 g).

mp: 135–136° C.
IR (CHCl$_3$) 1740 cm$^{-1}$.

EXAMPLE 16

Ethyl 3-(4-hydroxy-5-oxo-3-phenyl-2,5-dihydro-2furyl)propionate (11.3 g) was obtained according to a similar manner to that of Example 15.

mp: 116–118° C.
IR (CHCl$_3$): 3490, 1740 cm$^{-1}$.

EXAMPLE 17

A mixture of ethyl 3-(5-oxo-4-pentyloxy-3-phenyl-2,5-dihydro-2-furyl)propionate (3 g) and 3N hydrochloric acid (28 ml) in acetic acid (28 ml) was heated at 100° C. for 2 hours with stirring. After cooling the mixture was poured into water and extracted with ethyl acetate. The extract was washed with water and brine successively and dried. Evaporation of the solvent gave a residue which was recrystallized from a mixture of n-hexane and ethyl acetate to give 3-(5-oxo-4-pentyloxy-3-phenyl2,5-dihydro-2-furyl)propionic acid (2.20 g).

mp: 86–87° C.
IR (Nujol) : 2650, 1755, 1710, 1655 cm$^{-1}$.
NMR (CDCl$_3$, δ): 0.73–2.10 (10H, m), 2.20–3.00 (3H, m), 4.20–4.70 (2H, m), 5.50 (1H, dd, J=2, 8 Hz), 7.33–7.90 (5H, m), 9.67 (1H, br s).

EXAMPLE 18

3-(4-Methoxy-5-oxo-3-phenyl-2,5-dihydro-2-furyl)-propionic acid was obtained according to a similar manner to that of Example 17.

mp 126–127° C.
IR (CHCl$_3$): 1750, 1710 cm$^{-1}$.
NMR (CDCl$_3$, δ): 1.5–2.1 (1H, m), 2.2–2.9 (3H, m), 4.10 (3H, s), 5.43 (1H, dd, J=2, 8 Hz), 7.3–7.8 (5H, m), 9.57 (1H, br s).

EXAMPLE 19

3-[3-(4-Chlorophenyl)-4-methoxy-5-oxo-2,5-dihydro-2-furyl]propionic acid was obtained according to a similar manner to that of Example 17.

mp : 142°–143° C.
IR (Nujol) : 3100, 1730, 1710, 1640 cm$^{-1}$.
NMR (CDCl$_3$, δ): 1.48–1.93 (1H, m), 2.20–2.78 (3H, m), 4.13 (3H, s), 5.43 (1H, dd, J=2, 8 Hz), 7.45 (2H, d, J=9 Hz), 7.63 (2H, d, J=9 Hz), 8.33 (1H, br s).

EXAMPLE 20

3-[4-Methoxy-5-oxo-3-(3-trifluoromethylphenyl)2,5-dihydro-2-furyl]propionic acid was obtained according to a similar manner to that of Example 17.

mp: 131.5°–132.5° C.
IR (Nujol) : 1760, 1700; 1645 cm$^{-1}$.
NMR (CDCl$_3$, δ): 1.48–1.90 (1H, m), 2.20–2.83 (3H, m), 4.18 (3H, s), 5.50 (1H, dd, J=2, 9 Hz), 7.90 (1H, br s), 7.50–8.10 (4H, m).

EXAMPLE 21

4-(4-Methoxy-5-oxo-3-phenyl-2,5-dihydro-2-furyl)-butyric acid was obtained according to a similar manner to that of Example 17.

mp: 94°–96° C.
IR (CHCl$_3$): 1750, 1705 cm$^{-1}$.
NMR (CDCl$_3$, δ): 1.5–2.0 (4H, m), 2.1–2.6 (2H, m), 4.03 (3H, s), 5.33 (1H, dd, J=2, 8 Hz), 7.3–7.7 (5H, m), 10.50 (1H, br s).

EXAMPLE 22

To a solution of methyl 3-(4-ethoxy-5-oxo-3-phenyl2,5-dihydro-2-furyl)propionate (0.20 g) in methanol (2 ml) was added 1N sodium hydroxide solution (0.8 ml) during a period of a few minutes at ambient temperature. The solution was stirred for 30 minutes at the same temperature and then poured into water (10 ml). The mixture was washed with diethyl ether and the aqueous layer was adjusted to pH 1 with aqueous 10% hydrochloric acid. The separated oil was extracted with ethyl acetate twice. The combined organic layers were washed with water three times, dried, and evaporated to dryness. The residue was crystallized from a mixture of diethyl ether and n-hexane to yield 3-(4-ethoxy-5-oxo-3-phenyl2,5-dihydro-2-furyl)propionic acid (121 mg) as a crystal.

mp: 114°–116° C.

IR (Nujol) : 1755, 1710, 1645 cm$^{-1}$.

NMR (DMSO-d$_6$, $\delta$): 1.27 (3H, t, J=7 Hz), 1.40-2.25 (4H, m), 4.38 (2H, q, J=7Hz), 5.69 (1H, q, J=1.5, 9Hz), 7.33–7.90 (5H, m).

EXAMPLE 23

3-(4-Propoxy-5-oxo-3-phenyl-2,5-dihydro-2-furyl)-propionic acid (77 mg) was obtained according to a similar manner to that of Example 22.

mp: 123°–125° C.

IR (CHC13) : 1755, 1705 cm$^{-1}$.

Mass: 290 (M+).

EXAMPLE 24

3-(4-Butoxy-5-oxo-3-phenyl-2,5-dihydro-2-furyl)propionic acid (58 mg) was obtained according to a similar manner to that of Example 22.

mp: 94°–96° C.

IR (CHC13) : 2700-2400, 1750, 1705 cm$^{-1}$.

Mass: 304 (M+).

EXAMPLE 25

5-(2-Benzyloxyethyl)-3-methoxy-4-phenyl-2(5H)furanone (2.06 g) was dissolved in methanol (20 ml), and palladium black (20 mg) was added. Catalytic reduction was carried out in ordinary temperature and atmosphere. After completion of the reaction, the palladium black was filtered off and the methanol was distilled off under reduced pressure. The crude crystals thus obtained were recrystallized from chloroform to give 3-methoxy-5-(2-hydroxyethyl)-4-phenyl-2(5H)-furanone (1.345g).

IR (CH$_2$Cl$_2$): 3600, 1755 cm$^{-1}$.

NMR (DMSO-d$_6$, $\delta$): 1.2–2.3 (2H, m), 3.4–3.8 (2H, m), 4.0 (3H, s), 5.70 (1H, dd, J=3, 8 Hz), 7.3–7.8 (5H, m).

EXAMPLE 26

To a solution of 3-(4-methoxy-5-oxo-3-phenyl-2,5-dihydro-2-furyl)propionic acid (3 g) and triethylamine (1.95 ml) in tetrahydrofuran was added dropwise isobutyl chloroformate (1.79 ml) at −20° C. with stirring and the mixture was stirred for 40 minutes at the same temperature. To this mixture was added sodium borohydride (1.11 g) at −20° C. and the mixture was stirred for 3 hours at ambient temperature. After being acidified with 10% hydrochloric acid at 0° , the solvent was removed under the reduced pressure to give a residue which was poured into water and extracted with diethyl ether. The ethereal extract was washed with 1N hydrochloric acid and saturated aqueous solution of sodium bicarbonate successively and dried. Evaporation of the solvent gave an oil which was chromatographed on silica gel in chloroform to give 5-(3-hydroxypropyl)-3-methoxy-4- phenyl-2(5H)-furanone (2.35 g) as an oil.

IR (Nujol): 3400, 1745, 1645 cm$^{-1}$.

NMR (CDCl$_3$, $\delta$): 1.43–2.33 (5H, m), 3.50–3.83 (2H, t, J=6 Hz), 4.07 (3H, s), 5.42 (1H, dd, J=3, 8 Hz), 7.35–7.77 (5H, m).

EXAMPLE 27

2N Jones reagent (8 ml) was diluted with acetone (12.5 ml). To this solution was added a solution of 5-(2-hydroxyethyl)-3-methoxy-4-phenyl-2(5H)-furanone (1.25 g) in acetone (12.5 ml) at 0° C. over a period of 50 minutes. The mixture was stirred at ambient temperature for 15 minutes and isopropylalcohol (5 ml) was added thereto. The mixture was poured into a mixture of ethyl acetate and water. The organic layer was separated, washed with water and brine, and dried. Evaporation of the solvent gave 2-(2,5-dihydro-4-methoxy-5-oxo-3-phenyl-2-furyl)acetic acid (865 mg) which was recrystallized from diethyl ether.

mp: 159°–160° C.

IR (Nujol) : 1760, 1695, 1655 cm$^{-1}$.

NMR (DMSO-d$_6$, $\delta$): 2.40 (1H, dd, J=8, 17 Hz), 2.87 (1H, dd, J=3, 17 Hz), 3.95 (3H, s), 5.88 (1H, dd, J=3, 8 Hz), 7.4–7.7 (5H, m).

EXAMPLE 28

To a solution of 5-(4-diazo-3-oxobutyl)-3-methoxy-4-phenyl-2(5H)-furanone (100 mg) in methanol (2 ml) was added dropwise a solution of silver benzoate (9.6 mg) in triethylamine (0.2 ml) over a period of 10 minutes at 0° C. with stirring and the mixture was stirred for 30 minutes at ambient temperature. The reaction mixture was filtered off and the filtrate was condensed and dituted with diethyl ether. The ethereal solution was washed with 1N hydrochloric acid, water and brine successively and dried. Evaporation of the solvent gave methyl 4-(4-methoxy-5-oxo-3-phenyl-2,5-dihydro2-furyl)butyrate (100 mg) as an oil.

IR (CHCl$_3$): 1750, 1645 cm$^{-1}$.

NMR (CDCl$_3$, $\delta$): 1.4–2.2 (4H, m), 2.33 (2H, t, J=6 Hz), 3.62 (3H, s), 4.07 (3H, s), 5.35 (1H, dd, J=2, 8 Hz), 7.3–7.7 (5H, m).

EXAMPLE 29

(1) Sodium (0.64 g) was added to ethanol (30 ml) at ambient temperature, followed by dimethyl malonate (3.2 ml), and the resulting mixture was stirred at ambient temperature for 15 minutes. A solution of (2R*, 3R*)-3-[3-(t-butyldiphenylsilyloxy)propyl]-2phenyloxirane (2.90 g) in ethanol (30 ml) was added thereto. After being refluxed for 12 hours, the reaction mixture was evaporated in vacuo and the residue was dissolved in ethyl acetate. The organic solution was washed with 1N hydrochloric acid, water and brine successively, dried over magnesium sulfate, and evaporated in vacuo. The residue was chromatographed on silica gel (150 g) eluting with a mixture of hexane and ethyl acetate (50:1 to 10:1) to give ethyl (4R*,5R*)5-[3-(t-butyldiphenylsilyloxy)propyl]-2-oxo-4-phenyltetrahydro-3-furancarboxylate (2.64 g).

IR (film): 1780, 1735 cm$^{-1}$.

NMR (CDCl$_3$, $\delta$): 0.97 (9H, s), 1.2–2.0 (7H, m), 3.5–4.7 (6H, m), 7.1–7.8 (15H, m).

(2) A mixture of ethyl (4R*,5R*)-5-[3-t-butyldiphenylsilyloxy)propyl]-2-oxo-4-phenyltetrahydro-3furancarboxylate (2.43 g) in ethanol (40 ml) and 1N aqueous sodium hydroxide (9.16 ml) was stirred at 50° C. for 2 hours. 1N HYdrochloric acid (10 ml) was added to the reaction mixture and the organic solvent was evaporated in vacuo. The aqueous solution was extracted with ethyl acetate, and the extract was washed with water and brine, dried over magnesium sulfate, and evaporated in vacuo to give (4R*,5R*)-5-[3-t-butyldiphenylsilyloxy)propyl]-2-oxo-4-phenyltetrahydrofuran-3-carboxylic acid (2.20 g) as an oil.

IR (film): 1780, 1730 cm$^{-1}$.

NMR (CDCl$_3$, δ) : 1.98 (9H, s), 1.0–1.8 (4H, m), 3.56 (2,, t, J=4 Hz), 3.7–4.4 (2H, m), 5.0 (1H, d, J=6 Hz), 7.0–7.8 (15H, m).

(3) A solution of (4R*,5R*)-5-[3-t-butyldiphenylsilyloxy)propyl]2-oxo-4-phenyltetrahydrofura acid (1.71 g) was heated to 00° C. for 3 hours. The reaction mixture was evaporated and the residue was chromatographed on silica gel (25 g) eluting with benzene to give (4R*,5R*)-5-[3-t-butyldiphenylsilyloxy)propyl] -2-oxo-4-phenyltetrahydrofuran, which was crystallized from hexane (510 mg).

IR (film): 1775 cm$^{-1}$.

NMR (CDCl$_3$, δ): 0.96 (9H, s), 1.2–1.8 (4H, m), 2.80 (2H, t, J=8Hz), 3.4–3.8 (3H, m), 4.64 (1H, d, J=6Hz), 7.0–7.7 (15H, m).

(4) 1N Solution of lithium bistrimethylsilylamide in tetrahydrofurane (1.55 ml) was added to a solution of (4R*,5R*)-5-[3-(t-butyldiphenylsilyloxy)propyl]-2-oxo4-phenyltetrahydrofuran (645 mg) in tetrahydrofuran (13 ml) at −70° C., and the resulting mixture was stirred at −70° C. for 30 minutes and allowed to warm to −20° C. over 20 minutes. The mixture was cooled to −70° C. and a solution of diphenyl disulfide (338 mg) in tetrahydrofuran (3.04 ml) was added thereto. After stirring at −70° C. for 30 minutes, the mixture was poured into a mixture of diethyl ether and 0.5N hydrochloric acid. The organic layer was separated, washed with water and brine, dried over magnesium sulfate and evaporated in vacuo. The residue was chromatographed on silica gel eluting with a mixture of benzene and acetone (50:1 to 10:1) to give (3R*,4S*,5R*)-5-[3-(t-butyldiphenylsilyloxy)propyl] -2-oxo-4-phenyl-3-phenylthiotetrahydrofuran (666 mg) as an oil.

IR (CH ): 1765 cm$^{-1}$.

NMR (CDCl$_3$, δ) : 0.96 (9H, s), 1.2–1.7 (4H, m), 3.53 (2H, t, J=5 Hz), 3.5–4.2 (2H, m), 4.00 (lH, d, J=5.5 Hz), 7.2–7.7 (20H, m).

(5) m-Chloroperbenzoic acid (242 mg) was added to a solution of (3R*,4S*,5R*)-5-[3-(t-butyldiphenylsilyloxy)propyl] -2-oxo-4-phenyl-3-phenylthiotetrahydrofuran in dichloromethane (10 ml) at 0° C. and the resulting mixture was stirred at 0° C. for 30 minutes. The resulting mixture was poured into a mixture of diethyl ether, aqueous sodium bisulfite and aqueous sodium bicarbonate. The organic layer was separated, washed with water and brine successively, dried over ( magnesium sulfate, and evaporated in vacuo to give (3R*,4S*,5R*)-5-[3-(t-butyldiphenylsilyloxy)propyl]-2(oxo-4-phenyl-3-phenylsulfinyltetrahydrofuran (537 mg) as an oil.

(6) A solution of (3R*,4S*,5R*)-5-[3-(t-butyldiphenylsilyloxy)propyl]-2-oxo-4-phenyl-3- phenylsulfinyltetrahydrofuran (650 mg) in toluene (6.5 ml) was refluxed for 30 minutes. The reaction mixture was chromatographed on silica gel (20 g) eluting with a mixture of benzene and acetone (100:1 to 25:1) to give 5-[3-(t-butyldiphenylsilyloxy)propyl]-4-phenyl-2(5H)furanone (313 mg) as an oil.

IR (CH 1750 cm$^{-1}$.

NMR (CDCl$_3$, δ) : 1.00 (9H, s), 1.4–2.2 (4H, m), 3.63 (2H, t, J=5 Hz), 5.53 (1H, dd, J=2, 8 Hz), 6.25 (1H, s), 7.2–7.7 (15H, m).

(7) 1M Solution of tetrabutylammonium fluoride in tetrahydrofuran (0.736 ml) was added to a solution of 5-[3-(t-butyldiphenylsilyloxy)propyl]-4-phenyl-2(5H)-furanone (280 mg) in tetrahydrofuran (3 ml) and the resulting mixture was stirred at same temperature for 3 hours. The reaction mixture was poured into a mixture of ethyl acetate and 0.5N hydrochloric acid. The organic layer was separated, washed with water and brine successively, dried over magnesium sulfate, and evaporated in vacuo to give 5-(3-hydroxypropyl)-4-phenyl-2(5H)-furanone (96 mg).

IR (CH 3600, 1750 cm$^{-1}$.

(8) A solution of 5-(3-hydroxypropyl)-4-phenyl2(5H)-furanone (90 mg) in acetone (1 ml) was added to a solution of 2N Jones reagent (0.62 ml) in acetone (1 ml) at 0° C. over 10 minutes, and the resulting mixture was stirred at 0° C. for 20 minutes. After addition of isopropyl alcohol (1 ml), the mixture was poured into a mixture of ethyl acetate (20 ml) and water (20 ml). The aqueous layer was separated and extracted with ethyl acetate (10 ml). The organic layers were combined, washed with water and brine sucсssively, dried over magnesium sulfate and evaporated in vacuo. The residue was chromatographed on silica gel (3 g) eluting with a mixture of chloroform and methanol (50:1 to 20:1) to give an oily product of 3-(2,5-dihydro5-oxo-3-phenyl-2-furyl)propionic acid, which was crystallized from diethyl ether (60 mg).

mp : 144–145° C.

IR (CH 3450, 1750, 1710 cm$^{-1}$.

NMR (CDC13, δ) : 1.7–2.1 (1H, m), 2.2–2.8 (3H, m), 5.82 (1H, dd, J=2, 8 Hz), 6.50 (1H, s), 7.4–7.8 (5H, m).

EXAMPLE 30
1) A soluton of 3-(4-hydroxy-5-oxo-3-phenyl-2,5-dihydro-2-furyl)propionic acid (6 g) and cinchonidine (7.14 g) in ethanol (1.3 l) was kept to stand at ambient temperature. The resultant crystal (10.08 g) was collected by filtration. The crystal was recrystallized from ethanol (the crystal: 7.95 g, the filtrate: 2.15 g). The resulting crystal (7.95 g) was taken up in ethyl acetate and the ethyl acetate solution was washed with 0.5N hydrochloric acid (twice) and water and dried. Evaporation of the solvent gave a crystal (3.35 g).

$[\alpha]_D^{21}$ = +48.93°±0.18° (C=1, MeOH).

This crystal (3.35 g) was dissolved in ethanol (330 ml) and to this solution was added a solution of quinine (4.8 g) in ethanol (100 ml). The precipitated crystal (3.14 g) was collected by filtration. This crystal was recrystallized from ethanol twice to give 3-(4-hydroxy-5-oxo-3-phenyl-2,5-dihydro-2-furyl)propionic acid quinine salt as prisms (1.30 g).

mp : 149–152° C 6;

$[\alpha]_D^{21}$ = −52.24° (C=1, MeOH).

The filtrate derived from the cinchonidine salt was condensed (6.16 g) and taken up in ethyl acetate and dilute hydrochloric acid. The ethyl acetate solution was washed with water and dried. Evaporation of the solvent gave a crystal (2.55 g).

$[\alpha]_D^{22}$ = −65.84° (C=1, EtOH).

The crystal was dissolved in ethanol (100 ml) and to this solution was added a solution (50 ml) of brucine 2H₂O (4.43 g). The precipitated crystal was collected by filtration (6.17 g). The crystal was recrystallized from ethanol four times to give 3-(4-hydroxy-5-oxo-3-phenyl-2,5-dihydro-2-furyl)propionic acid brucine salt (1.49 g).

mp : 140-142° C.

$[\alpha]_D^{21} = -53.52°$ (C=1, MeOH).

(2) 3-(4-Hydroxy-5-oxo-3-phenyl-2,5-dihydro-2-furyl)propionic acid quinine salt (1.15 g) was taken up in ethyl acetate and 0.5N hydrochloric acid and the organic solution was washed with 0.5N hydrochloric acid and water and dried. Evaporation of the solvent gave a residue which was recrystallized from a mixture of ethyl acetate and n-hexane to afford (d)-3-(4-hydroxy5-oxo-3-phenyl-2,5-dihydro-2-furyl)propionic acid (0.37 g) as prisms.

mp : 174.5-175.5° C.

$[\alpha]_D^{22} = +132.1°$ (C=1, EtOH).

(3) 3-(4-Hydroxy-5-oxo-3-phenyl-2,5-dihydro-2furyl)propionic acid brucin salt (1.362 g) was taken up in ethyl acetate and 0.5N hydrochloric acid and the organic solution was washed with 0.5N hydrochloric acid and water and dried. Evaporation of solvent gave a residue which was recrystallized from ethyl acetate n-hexane to afford (l)-3-(4-hydroxy-5-oxo-3-phenyl-2,5-dihydro-2-furyl)propionic acid (0.22 g) as prisms.

mp : 174.5-175.5° C.

$[\alpha]_D^{20} = -129.95°$ (C=1, EtOH).

What we claim is:

1. A compound of the formula:

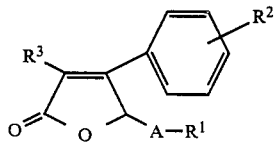

wherein

A is a lower alkylene group,

R₁ is a carboxy, hydroxy, benzyloxy, or lower alkoxycarbonyl group,

R² is a hydrogen or halogen atom or a halo(lower)alkyl group, and

R³ is a hydrogen atom or a hydroxy, carboxy, lower alkoxy or lower alkoxycarbonyl group, and pharmaceutically acceptable salts thereof.

2. The compound of claim 1, wherein

R¹ is a carboxy or lower alkoxycarbonyl group.

3. The compound of claim 2, which is ethyl 3-(4-methoxy-5-oxo-3-phenyl-2,5-dihydro-2-furyl)propionate.

4. A pharmaceutical aldose reductase inhibiting composition comprising an effective amount of a compound as defined in claim 1 or its pharmaceutically acceptable salt in admixture with an inert carrier.

5. A method for the treatment of diabetic cataract and/or neuropathy in a subject in need of such treatment which comprises administering to the subject an effective amount of a compound of the formula

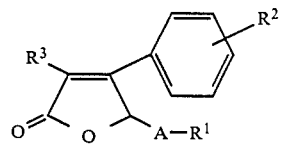

wherein

A is a lower alkylene group,

R¹ is a carboxy, hydroxy, benzyloxy, silyloxy or lower alkoxycarbonyl group,

R² is a hydrogen or ahlogen atom or a halo(lower)alkyl group, and

R³ is a hydrogen atom or a hydroxy, carboxy, lower alkoxy or lower alkoxycarbonyl group, and pharmaceutically acceptable salts thereof.

6. A method for the treatment of diabetic cataract and/or neuropathy in a subject in need of such treatment which comprises administering to the subject an effective amount of the compound ethyl 3-(4-methoxy-5-oxo-3-phenyl-2,5-dihydro-2-furyl)proprionate.

7. A method for the treatment of diabetic cataract ad/or neuropathy in a subject in need of such treatment which comprises administering to the subject an effective amount of the compound 3-(4-methoxy-5-oxo-3-phenyl-2,5-dihydro-2-furyl)priopionic acid.

8. The compound of claim 2, which is 3-(4-methoxy-5-oxo-3-phenyl-2,5-dihydro-2-furyl)propionic acid.

* * * * *